(12) United States Patent
Swanson et al.

(10) Patent No.: US 10,527,599 B2
(45) Date of Patent: Jan. 7, 2020

(54) METHOD AND KIT FOR DETERMINING IF A SHOCK TREATMENT IS NECESSARY FOR A WATER SOURCE

(71) Applicant: HACH COMPANY, Loveland, CO (US)

(72) Inventors: Teresa Lynn Swanson, Elkhart, IN (US); Ronald P. Merwin, Granger, IN (US)

(73) Assignee: HACH COMPANY, Loveland, CO (US)

(*) Notice: Subject to any disclaimer, the term of this patent is extended or adjusted under 35 U.S.C. 154(b) by 612 days.

(21) Appl. No.: 14/154,397

(22) Filed: Jan. 14, 2014

(65) Prior Publication Data

US 2015/0198575 A1 Jul. 16, 2015

(51) Int. Cl.
*G01N 33/18* (2006.01)
*G01N 31/22* (2006.01)

(52) U.S. Cl.
CPC ........... *G01N 33/182* (2013.01); *G01N 31/22* (2013.01); *Y10T 436/153333* (2015.01)

(58) Field of Classification Search
CPC .................................................. G01N 33/182
USPC ....................................................... 73/53.01
See application file for complete search history.

(56) References Cited

U.S. PATENT DOCUMENTS

| | | | |
|---|---|---|---|
| 4,904,605 A * | 2/1990 | O'Brien | G01N 33/18 356/421 |
| 5,491,094 A * | 2/1996 | Ramana | G01N 31/22 422/420 |
| 5,888,758 A | 3/1999 | Wu | |
| 5,976,823 A | 11/1999 | Wu | |
| 6,413,473 B1 * | 7/2002 | Bacon | G01N 21/78 422/408 |

(Continued)

FOREIGN PATENT DOCUMENTS

| | | |
|---|---|---|
| EP | 1 259 798 | 5/2002 |
| WO | WO2013/063654 | 5/2013 |

OTHER PUBLICATIONS

AquaChek Select "The Complete Guide to Pool and Spa Care", 2005.; whole document.*

(Continued)

*Primary Examiner* — Justin Seo
*Assistant Examiner* — Rodney T Frank
(74) *Attorney, Agent, or Firm* — Ference & Associates LLC

(57) ABSTRACT

A kit for determining if a shock treatment is required for a water source may comprise a test strip having at least two chemically treated test areas. One of the areas is responsive in color to a concentration of free chlorine in the water and another test area is responsive in color to a concentration of total chlorine in the water. A chlorine indicator scale may be provided on a substrate, such as a label, and comprises a plurality of pairs of colored indicia and each pair of colored indicia representing a color pattern indicating a concentration, or range of concentrations, of total chlorine and free chlorine in the water. An alphanumeric designation may be provided adjacent to each pair of indicia indicating whether a shock treatment is required for the water source based on a color pattern the associated indicia pattern.

15 Claims, 1 Drawing Sheet

(56) References Cited

U.S. PATENT DOCUMENTS 7,319,037 B1 * 1/2008 Albeck-Marom ..... G01N 31/22
422/412
2007/0287182 A1 * 12/2007 Morris ................... G01N 21/01
436/2

OTHER PUBLICATIONS

AquaChek, Hach, Water Quality Test Strips for Total Chlorine Free Chlorine, 1 pg.
AquaChek, Hach, Pro Pool & Spa Test Strips Each Strip Tests: Total Chlorine Total Bromine Free Chlorine pH Total Alkalinity, 1 pg.
APSP, The Association of Pool & Spa Professionals, American National Standard for Water Quality in Public Pools and Spas, Jun. 15, 2009, 13 pages.
EP Communication pursuant to Article 94(3) EPC, dated Mar. 27, 2018, 4 pages.

* cited by examiner

METHOD AND KIT FOR DETERMINING IF A SHOCK TREATMENT IS NECESSARY FOR A WATER SOURCE

BACKGROUND OF THE INVENTION

Embodiments of the invention pertain to systems and methods for testing chlorine content of a water source. More specifically, embodiments relate to chlorine testing systems and methods that utilize chemically treated test strips to determine an amount of free chlorine and total chlorine that are present in a water source.

Chlorine has been used to disinfect water in industrial applications since the early 1800's, and is widely used today for example to disinfect water in swimming pools and spas. Hydrochloric acid, hypochlorous acid and the hypochlorite ion are formed when chlorine is added to water. Chlorine existing in water in these acid and ion forms is known as "free chlorine" and is a bactericide available to kill bacteria, algae, and disease carrying or causing organisms. "Combined chlorine" is formed when free chlorine has killed the contaminants, which contain ammonia, in the water source. These chloramines may include monochloramine, dichloramine and nitrogen trichloride. Once free chlorine undergoes a reaction to form these combined chlorines, it is no longer effective as a sanitizer. "Total chlorine" is the sum of free chlorine plus combined chlorine. Thus, total chlorine may include 100% free chlorine, 100% combined chlorine or some ratio there between.

There are various systems and/or methods for testing the amount of free chlorine that is available in a water source. One such test method is OTO (ortho-toluidine), which is a liquid test method. In the presence of chlorine the OTO will turn a water sample yellow and the sample becomes a darker yellow as the amount of chlorine increases. Another test method is known as DPD, which is shorthand for N,N-diethyl-para-phenylenediamine. It is available as a liquid, powder or tablet type of test. There are several types of DPD test methods, but the most widely used is colorimetric DPD, whereby the N,N-diethyl-para-phenylenediamine is oxidized by chlorine creating a magenta color. The intensity of the color is directly proportional to concentration of chlorine in the water.

Still another method of testing water that is different from the liquid, powder, or tablets mentioned above, includes test strips. Test strips are similar to the DPD test in that they are designed, and able to test for free chlorine and chloramines. The test strips typically include two test areas on a substrate that are chemically treated with a chlorine indicator such as syringaldazine and/or tetramethylbenzidine (also known as TMB), which are color responsive to chlorine and chloramines.

Test strips are typically sold in a container that has a label on the container, or an insert within the container, that includes a color scale to determine or estimate a concentration of free chlorine in a water source relative to a concentration of total chlorine, total chlorine being the sum of both free and combined chlorine. These test strips are used by consumers and professionals to determine if it is necessary to "shock" treat a water source such as a swimming pool or spa. Shocking, also known as super chlorinating, is a regular maintenance step for a pool. This treatment keeps pool water safe and clean by adding three to five times the normal amount of chlorine, or other chemical sanitizer, to the pool water to drastically raise the chlorine level for a short time. This helps to remove ineffective chlorine amounts, kills bacteria and anything organic in the pool, and boosts the availability of effective or free chlorine.

A typical color scale for test strips is shown in FIG. 1 and includes two rows 10, 12 of colored blocks 14, 16, respectively. The blocks 14 of row 10 represent different concentrations of total chlorine as indicated by the color of a respective block. The blocks 16 of row 12 represent different concentrations of free chlorine as indicated by the color of a respective block. The colors of the blocks 14, 16 in each row range from white or off-white to a purple or a deep purple color. A number is below each block and each number indicates a concentration level of total chlorine or free chlorine in parts per million of a water sample tested.

The test strip is dipped into a water source and agitated within the water for a time period, e.g., 30 seconds. Once removed, the user of the test strip observes the color change of the test areas to determine the amount of total chlorine and the amount of free chlorine detected. The user then calculates the amount of combined chlorine present in the water source, by subtracting the concentration of free chlorine from the concentration of total. If the amount of combined chlorine exceeds the amount of free chlorine available in the water source, the user should shock treat the water source.

A drawback with this test strip test method is that consumers who maintain their own pool and/or spa may find this quantitative method confusing in terms of calculating the amount of combined chlorine in the pool relative to the amount of free chlorine available. Moreover, a consumer user may not understand or appreciate the differences between total, free and combined chlorine.

SUMMARY OF THE INVENTION

Embodiments of the invention provide a simple qualitative test method that does not require numeric calculations to determine whether or not it is necessary for a water shock treatment. Accordingly, embodiments may include a kit for determining if a shock treatment is required for a water source. The kit may comprise a test strip having at least two chemically treated test areas. One of the areas is responsive in color to a concentration of free chlorine in the water and another test area is responsive in color to a concentration of total chlorine in the water A chlorine indicator scale may be provided on a substrate, such as a label, and comprises a plurality of pairs of colored indicia and each pair of colored indicia representing a color pattern indicating a concentration, or range of concentrations, of total chlorine and free chlorine in the water. In an embodiment, the scale includes a first row of a plurality of different colored first indicia each color representing a concentration of total chlorine in the water. In addition, the scale includes a second row of a plurality of different colored second indicia each color representing a concentration of free chlorine in the water. Each first colored indicium is preferably aligned with a corresponding second colored indicia forming pairs of first and second colored indicia that provide a color indication of whether a shock treatment is required. An alphanumeric indication may be provided adjacent to each pair of first and second colored indicia indicating whether or not a shock treatment is required for the water source based on a color pattern of a corresponding pair of first and second colored indicia and without requiring a numeric calculation of relative concentrations of combined chlorine and free chlorine.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION OF THE INVENTION

Figure 1:
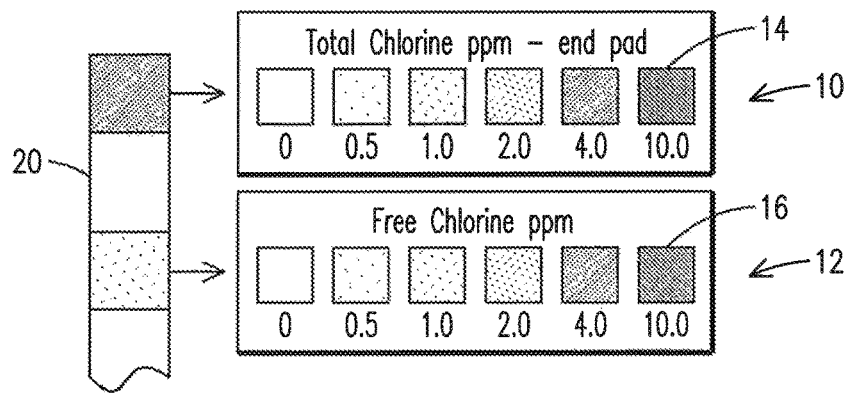
FIG. 1 is a prior art chlorine indicator scale.

Embodiments are described herein with reference to the attached figures wherein like reference numerals are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

Figure 2:
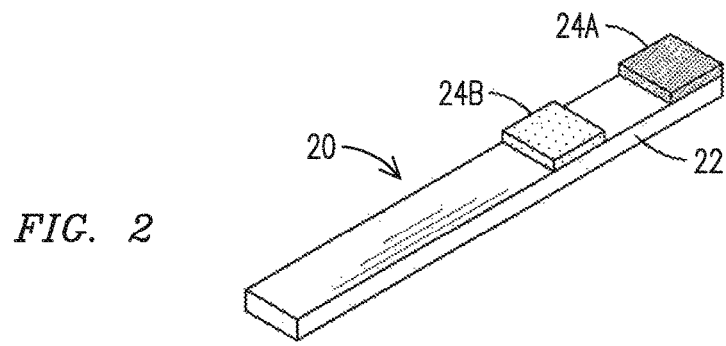
FIG. 2 is a perspective view of a test strip in accordance with embodiments of the invention.

With respect to FIG. 2, a test strip 20 is illustrated and includes a substrate 22 with two test areas 24A, 24B. The substrate 20 may include a generally hydrophobic material such as polystyrene. The test areas may be chemically treated with a reagent or indicator that is color responsive to chlorine present in a water source. By way of example, the test areas 24A, 24B may be treated with an alzadine and/or benzidine based indicator such as syringaldazine and/or tetramethylbenzidine. The test areas 24A, 24B may be chemically treated pads of water absorbent material, such as a cellulose-based material, that are affixed to the substrate 22 using known adhesive materials. However, depending on the nature or composition of the material of the substrate 22, the test areas 24A, 24B may be chemically treated portions of the substrate itself. Moreover, while the embodiment described herein shows two test areas, the embodiments are not so limited and may include more than two test areas.

Figure 3:
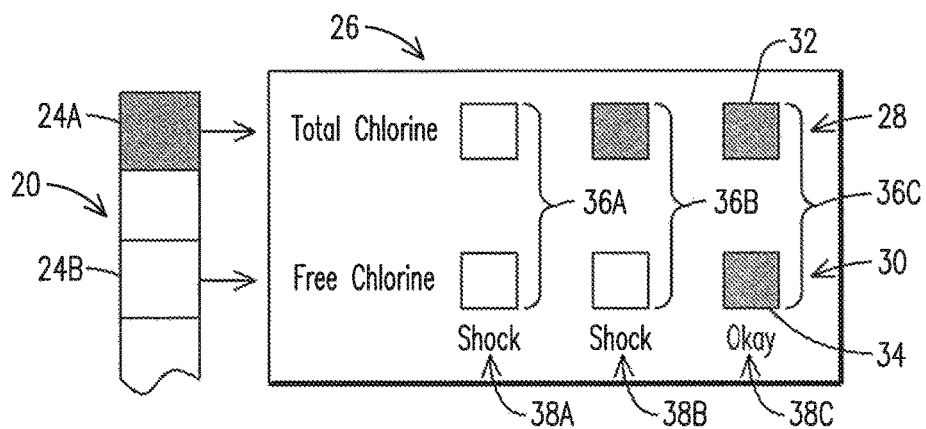
FIG. 3 is a chlorine indicator scale in accordance with embodiments of the invention.

In use when one desires to determine if a water source requires a shock treatment, the substrate 22, including the test areas 24A, 24B, is immersed in the water for a sufficient amount of time so that the test areas 24A, 24B are fully saturated with water. Once removed colors of the respective test areas 24A, 24B are compared to a chlorine indicator scale 26. A non-limiting example of such a scale 26 is illustrated in FIG. 3 and may include two rows 28, 30 of color coordinated indicia to provide an indication of whether or not a shock treatment is required for the water source.

The first or top row 28 includes first indicia 32, which represent an amount or amounts of total chlorine detected in a water source; and, the second or bottom row 30 includes second indicia 34, which represent an amount or amounts of free chlorine detected in the water source. Each first indicia 32 is associated with a second indicia 34 providing pairs 36A, 36B and 36C of indicia wherein each pair provides a color pattern indicating relative concentrations of the total chlorine and free chlorine detected in the water source. While the scale 26 shown in FIG. 3 includes three indicia 32 in each row 28, 30, the invention is not so limited. The scale 26 may include fewer or more indicia in each row. More indicia would provide more color patterns representing concentrations of free and total chlorine and more combinations indicating whether or not a shock treatment may be indicated.

In addition, alphanumeric instructions 38A, 38B and 38C regarding whether or not a shock treatment is necessary is provided below each respective pairs 36A, 36B and 36C of indicia. In the non-limiting example shown in FIG. 3, the pair 36A of indicia 32, 34 have a color pattern (e.g., white, off-white, pale yellow) that indicates the water source has very low concentrations of or no total chlorine and free chlorine. This color pattern indicates high levels of combined chlorine are present in the water. That is, the levels of total and free chlorine are so low that the color of the test areas 24A, 24 on the test strip 20 changed little, if any. Accordingly, the corresponding alphanumeric instruction 38A is "Shock" indicating a shock treatment is necessary.

The pair 36B of indicia 32, 34 has a color pattern that indicates that there is more combined chorine than free chlorine in the water source. That is, color of indicium 32 of pair 36B represents a concentration, e.g., 4 ppm, of total chorine and indicium 34 of the same pair 36B represents a concentration of free chlorine, e.g., 1 ppm of free chlorine that necessarily means there is more combined chlorine than free chlorine in the water source. However, a numeric calculation of the concentration of combined chlorine is not necessary as the scale 26 includes the instruction 38B to "Shock" indicating a shock treatment is necessary. In both of the above described instances when a shock treatment is designated as required, one will have to introduce chlorine into the water source to raise or increase the concentration of free chlorine to a predetermined level as necessary to kill any harmful contaminants or organisms.

Again in reference to FIG. 3, the pair 36C of indicia 32, 34 have colors indicating that there are generally equal amounts of total chlorine and free chlorine in the water source, which indicates that there is more free chlorine than combined chlorine in the water source. Accordingly, the instruction 38C is "Okay" or some other indication that a shock treatment is not likely required. However, a user could still choose to perform a shock treatment if he/she desired.

Embodiments may be provided in the form of a kit, wherein the test strip 20, or a plurality of test strips 20, is provided in a container. A label may be provided on the container that includes the above-described scale 26, or the scale 26 may be displayed on a sheet that is not on the container, but may be included for example as an insert in the container. In this manner, a person may remove a test strip 20 from the container to wet the test areas 24A, 24B and observe a color change, if any, of the test area indicating an amount or amounts of total chlorine and free chlorine present in a water source. Comparing the wetted test strips to the color patterns of the indicia pairs 36A, 36B, 36C on the scale 26, a user may simply follow the instructions 38A, 38B, 38C regarding whether or not to shock treat the water source, without the need to calculate an amount of combined chlorine in the tested water for comparison to an amount of free chlorine detected in the water.

The colors used or selected for indicia 32, 34 of pairs 36A and 36B represent relative concentration levels, or a range of concentration levels, that represent concentrations of free chlorine and total chlorine at which, or below which, it is assumed there is more combined chlorine than free chlorine in the water source, if any total chlorine is detected For example, with respect to indicia pair 36A the colors represent that there is little if any free chlorine and total chlorine, thereby requiring shock treatment. Indicia pair 36B represents relative concentration levels of total chlorine detected, but the concentration level of free chlorine is at such a level that it is assumed that the concentration of combined total chlorine is greater than that of free chlorine. In a non-limiting example, the color of indicium 32 of pair 36B may represent a concentration of 10 ppm of total chlorine, and the color of indicium 34 of that pair may represent a concentration of 4 ppm, or lower, of free chlorine.

The color pattern of indicia pair 36C represent a concentration level, or a range of concentrations, of free chlorine and total chlorine, whereby it is assumed that there is more free chlorine than combined chlorine. That is, the color of indicia 34 of pair 36C may represent a concentration of free chlorine, depending on the amount of recommended free chlorine initially provided in the water source, at which or above which there must be more free chlorine than total chlorine. In a non-limiting example, for a recommended maximum concentration of free chlorine of 10 ppm, the color of indicia 34 may represent a concentration of 6 ppm of free chlorine or greater, in which case there will be a lesser amount of combined chlorine. However, given the color patterns and the alphanumeric indicators, a calculation of combined chlorine is not necessary.

While embodiments have been described with reference to various embodiments, it will be understood by those skilled in the art that various changes, omissions and/or additions may be made and equivalents may be substituted for elements thereof without departing from the spirit and scope of the embodiments. In addition, many modifications may be made to adapt a particular situation or material to the teachings of the embodiments without departing from the scope thereof. Therefore, it is intended that the embodiments not be limited to the particular embodiment disclosed as the best mode contemplated, but that all embodiments falling within the scope of the appended claims are considered. Moreover, unless specifically stated, any use of the terms first, second, etc., does not denote any order or importance, but rather the terms first, second, etc., are used to distinguish one element from another.

The invention claimed is:

1. A kit for determining if a shock treatment is required for a water source, comprising:
   one or more test strips having at least two chemically treated test areas and one area is responsive in color to a concentration of free chlorine in the water and the other test area is responsive in color to a concentration of total chlorine in the water;
   a chlorine indicator scale on a substrate, wherein the chlorine indicator scale does not include numeric values and comprising:
      three pairs of colored indicia comprising three columns and two rows, wherein a first row comprises three colored first indicia and wherein a second row comprises three colored second indicia, wherein each pair comprises a first indicia from the first row and a corresponding second indicia from the second row, the corresponding second indicia being located and aligned directly below the first indicia, wherein a first of the pairs comprises a first colored indicia color and a corresponding second colored indicia color representing low or no concentrations of total chlorine and free chlorine in the water, wherein a second of the pairs comprises a first colored indicia color and a second colored indicia color representing a concentration of total chlorine greater than a concentration of free chlorine in the water, and a third of the pairs comprises a first colored indicia color and a second colored indicia color representing substantially equal concentrations of total chlorine and free chlorine in the water, and wherein the color pattern of each pair is indicative of whether a shock treatment is required;
      the three colored first indicia of the first row each representing a relative concentration of total chlorine in the water, wherein a first of the first indicia indicates no or a low concentration of total chlorine in the water and wherein a second of the first indicia and a third of the first indicia indicates an other than no or low level of total chlorine in the water;
      the three colored second indicia each representing a relative concentration of free chlorine in the water, wherein a first of the second indicia and a second of the second indicia indicates no or a low concentration of free chlorine in the water and wherein a third of the second indicia indicates an other than no or low level of free chlorine in the water;
   and
   an alphabetical designation adjacent to each pair of first and second indicia, wherein the alphabetical designation adjacent to the first of the pairs and the second of the pairs comprises a term "shock" indicating a shock treatment is required for the water without requiring a numeric calculation of a concentration of combined chlorine and wherein the alphabetical designation adjacent to the third of the pairs indicates a shock treatment is not required for the water without requiring a numeric calculation of a concentration of combined chlorine.

2. The kit of claim 1, wherein the colors of the first pair of indicia are the same, and the colors of the second pair of indicia are different, and the colors of the third pair of indicia are the same but different than the colors of the first pair of indicia.

3. The kit of claim 2, wherein the color of the first indicia of the first and second pairs of indicia are different, and the color of the first indicia of the second and third pairs of indicia are the same; and the color of the second indicia of the first and second pairs of indicia are the same, and the color of the second indicia of the second and third pairs of indicia are different.

4. The kit of claim 1, wherein each of the one or more test strips comprises a substrate composed of substantially hydrophobic material, and the test areas each comprises a test pad composed of a water absorbent material that is fixed to the substrate and each test pad is treated with a chemical reagent that is responsive in color to free chlorine or total chlorine in the water source.

5. The kit of claim 1, wherein the alphabetical designation corresponding to each pair of first and second indicia is located and aligned directly below the second indicia of the pair.

6. The kit of claim 1, further comprising a container housing the one or more test strips.

7. The kit of claim 6, wherein the chlorine indicator scale is provided on the container.

8. The kit of claim 6, wherein the chlorine indicator scale is on a sheet housed within the container.

9. A kit for determining if a shock treatment is required for a water source, comprising:
   one or more test strips having at least two chemically treated test areas and one area is responsive in color to a concentration of free chlorine in the water and the other test area is responsive in color to a concentration of total chlorine in the water;
   a chlorine indicator scale on a substrate, wherein the chlorine indicator scale does not include numeric values and comprising:
      three pairs of colored indicia and each colored indicia representing a color pattern indicating a concentration, or range of concentrations, of total chlorine and free chlorine in the water, the three pairs of colored indicia comprising three columns and two rows, wherein a first row comprises three colored first indicia and wherein a second row comprises three colored second indicia, wherein each of the three pairs comprises a first indicia from the first row located and aligned above a corresponding second indicia and wherein a first of the three pairs comprises a first colored indicia color and a corresponding second colored indicia color representing low or no concentrations of total chlorine and free chlorine in the water, wherein a second of the three pairs comprises a first colored indicia color and a corresponding second colored indicia color representing a concentration of total chlorine greater than a concentration of free chlorine in the water, and a third of the three pairs comprises a first colored indicia color and a corresponding second colored indicia color representing substantially equal concentrations of total chlorine and free chlorine in the water; and
      an alphabetical designation adjacent to each pair of indicia, wherein the alphabetical designation adjacent to the first of the three pairs and the second of the three pairs comprises a term "shock" indicating a shock treatment is required for the water without requiring a numeric calculation of a concentration of combined chlorine and wherein the alphabetical designation adjacent to the third of the three pairs indicates a shock treatment is not required for the water without requiring a numeric calculation of a concentration of combined chlorine.

10. The kit of claim 9, wherein the pairs of indicia comprise:
   a first row of a plurality of colored first indicia; and
   a second row of a plurality of colored second indicia;
   wherein each first colored indicia is aligned with a corresponding second colored indicia forming pairs of first and second colored indicia and each pair provides a color pattern indicative of whether a shock treatment is required.

11. The kit of claim 9, wherein the colors of the first pair of indicia are the same, and the colors of the second pair of indicia are different, and the colors of the third pair of indicia are the same but different than the colors of the first pair of indicia.

12. The kit of claim 11, wherein the color of the first indicia of the first and second pairs of indicia are different, and the color of the first indicia of the second and third pairs of indicia are the same; and,
   the color of the second indicia of the first and second pairs of indicia are the same, and the color of the second indicia of the second and third pairs of indicia are different.

13. A method for determining if a shock treatment is required for a water source, comprising:
   wetting a test strip with water, wherein the test strip has at least two chemically treated test areas and one area is responsive in color to free chlorine in the water and the other test area is responsive in color to a total amount of chlorine in the water;
   referring to a chlorine indicator scale on a substrate, wherein the chlorine indicator scale does not include numeric values and comprising:
      three pairs of colored indicia and each colored indicia representing a color pattern indicating a concentration, or range of concentrations, of total chlorine and free chlorine in the water, the three pairs of colored indicia comprising three columns and two rows, wherein a first row comprises three colored first indicia and wherein a second row comprises three colored second indicia, wherein each of the three pairs comprises a first indicia from the first row located and aligned above a corresponding second indicia and wherein a first of the three pairs comprises a first colored indicia color and a corresponding second colored indicia color representing low or no concentrations of total chlorine and free chlorine in the water, wherein a second of the three pairs comprises a first colored indicia color and a corresponding second colored indicia color representing a concentration of total chlorine greater than a concentration of free chlorine in the water, and a third of the three pairs comprises a first colored indicia color and a corresponding second colored indicia color representing substantially equal concentrations of total chlorine and free chlorine in the water; and
      an alphabetical designation adjacent to each pair of first and second indicia, wherein the alphabetical designation adjacent to the first of the pairs and the second of the pairs comprises a term "shock" indicating a shock treatment is required for the water based on a color pattern of the pair of first and second indicia and wherein the alphabetical designation adjacent to the third of the pairs indicates a shock treatment is not required for the water based on a color pattern of the third of the pairs of first and second colored indicia;
   identifying which pair of first and second indicia on the substrate represents the colors of the test pads on the test strip to determine whether a shock treatment is required as set forth in the alphabetical indication adjacent to the identified pair of first and second indicia, without calculating a concentration of combined chlorine.

14. The method of claim 13, further comprising the step, when a shock treatment is determined necessary, introducing chlorine into the water source to increase the concentration of free chlorine in the water source.

15. The method of claim 13, wherein the pairs of indicia comprise:
   a first row of a plurality of colored first indicia; and
   a second row of a plurality of colored second indicia;
   wherein each first colored indicia is aligned with a corresponding second colored indicia forming pairs of first and second colored indicia and each pair provides a color pattern indicative of whether a shock treatment is required.

* * * * *